United States Patent
Shoji et al.

(10) Patent No.: US 6,660,148 B2
(45) Date of Patent: Dec. 9, 2003

(54) ELECTROPHORETIC METHOD AND ELECTROPHORETIC INSTRUMENT THEREFOR

(75) Inventors: Tomohiro Shoji, Hitachinaka (JP); Yoshiyuki Okishima, Minori-machi (JP); Masaya Kojima, Mito (JP); Muneo Maeshima, Mito (JP)

(73) Assignee: Hitachi, Ltd., Tokyo (JP)

( * ) Notice: Subject to any disclaimer, the term of this patent is extended or adjusted under 35 U.S.C. 154(b) by 208 days.

(21) Appl. No.: 09/793,242

(22) Filed: Feb. 26, 2001

(65) Prior Publication Data

US 2001/0017263 A1 Aug. 30, 2001

(30) Foreign Application Priority Data

Feb. 28, 2000 (JP) .......................... 2000-056042

(51) Int. Cl.$^7$ ..................... G01N 27/447; G01N 27/453
(52) U.S. Cl. ........................ 204/455; 204/605
(58) Field of Search ................ 204/451, 453, 204/455, 601, 604, 605

(56) References Cited

U.S. PATENT DOCUMENTS 5,635,050 A * 6/1997 Pentoney et al. ........... 204/605
6,383,356 B1 * 5/2002 Hayashizaki et al. ....... 204/605

FOREIGN PATENT DOCUMENTS

JP    11-511555    10/1999

* cited by examiner

*Primary Examiner*—Nam Nguyen
*Assistant Examiner*—Alex Noguerola
(74) *Attorney, Agent, or Firm*—Kenyon & Kenyon (57) ABSTRACT

An injection syringe 14 for injecting a gel into a capillary 111, a charging syringe 15 for charging the injection syringe 14 with the gel 10 are attached to a block 17. A check valve 16 is inserted between the both syringes, and the check valve 16 works so as to prevent the gel 10 from flowing back to the charging syringe 15. As the result, the gel charging can be automated, and accordingly the processing ability of the electrophoretic instrument can be improved.

12 Claims, 7 Drawing Sheets

ELECTROPHORETIC METHOD AND ELECTROPHORETIC INSTRUMENT THEREFOR

BACKGROUND OF THE INVENTION

1. Field of the Invention

The present invention relates to an electrophoretic instrument, and particularly to an electrophoretic instrument using a capillary filled with a gel of a medium for separating samples as an electrophoretic lane.

2. Prior Art

The PCT Japanese patent publication No. 11-511555 discloses a replacing means in which the old gel inside a capillary of a gel replacing system is replaced by the new gel delivered by a pump.

In the prior art described above, the manual operation to open the valve inserted between the charging syringe and the injection syringe when the injection syringe is charged with the gel. Therefore, the measurement must be temporarily suspended, and as the result, processing ability of the analysis is lowered.

Further, in the PCT Japanese patent publication No. 11-511555, there is no description on automatic gel charging during measurement.

SUMMARY OF THE INVENTION

An object of the present invention is to provide an electrophoretic method and an electrophoretic instrument which can perform gel charging during continuous analysis, and accordingly can improve the processing ability of analysis.

In order to attain the above object, according to one aspect of the present invention, there is provided an electrophoretic instrument which comprises a gel injection mechanism for injecting a gel of a medium for separating samples into one or more capillaries; and a check-valve for preventing backflow of the gel to a gel charging syringe arranged between a gel injection syringe and the gel charging syringe.

In the present invention, a polymer gel is used as the electrophoretic separation medium, and a labeled sample to be analyzed is moved in the polymer gel of electrophoretic separation medium during performing electrophoresis.

According to another aspect of the present invention, there is provided an electrophoretic instrument comprising a capillary; a gel injection mechanism for injecting a gel of a medium for separating a sample into the capillary; and a detection unit for optically detecting elctrophoretically separated compositions of the sample introduced into the capillary, wherein the gel injection mechanism comprises an injection syringe for injecting the gel into the capillary; a charging syringe for charging the injection syringe with the gel; a block having a flow passage connecting the both syringes, the capillary and a buffer reservoir; and a check valve for preventing the gel from flowing back to the charging syringe. It is preferable that the check valve described above is constructed so as to prevent the gel from flowing back to the charging syringe when the gel is injected from the injection syringe into the capillary. It is preferable that the flow passage of the block is composed of a first flow passage communicating between the charging syringe and the injection syringe; and a second flow passage for communicating between the injection syringe and the capillary. It is preferable that a branching passage to the buffer reservoir, into which an electrode used at performing electrophoresis is inserted, is provided at a middle position of the second flow passage. The examples of concrete structures are as follows.

(1) An electrophoresis method comprising the steps of supplying a gel for electrophoresis to a bore of an injection syringe; driving a plunger of the injection syringe by a motor; injecting the gel into a bore of a capillary through a block having a flow passage communicating to the capillary; and supplying an analyzed sample to the capillary to separate the sample by electrophoresis, the method further comprising the steps of detecting an amount of the gel remaining in the injection syringe; driving a plunger of a charging syringe to charge the flow passage in the block with the gel when the value of amount is smaller than a predetermined amount of the gel, the charging syringe being connected to the flow passage in the block through a check valve; then supplying the gel to the capillary by the plunger of the injection syringe.

(2) The electrophoresis method, wherein the capillary is a capillary array having a plurality of capillaries, and a sample is electrophoretically moved from sample supply ends serving as a cathode of the capillaries toward a buffer reservoir serving as an anode.

(3) The electrophoresis method further comprising the steps of obtaining amounts of the gel in the injection syringe and the charging syringe using encoders; injecting an amount of the gel necessary for once of the electrophoresis into the capillaries; then checking an amount of the gel remaining in the injection syringe; and supplying an amount of the gel necessary for the second and thereafter electrophoreses from the charging syringe into the injection syringe as required.

(4) The electrophoresis method further comprising the steps of exciting the sample separated by the electrophoresis using an electromagnetic wave; and detecting fluorescence generated by the excitation.

(5) An electrophoretic instrument comprising a capillary; a gel injection mechanism for injecting a gel of a sample separating medium into the capillary; a detecting unit for detecting a sample introduced into the capillary and electrophoretically separated; an injection syringe with a plunger for injecting the gel into the capillary; a charging syringe with a plunger for performing charging with the gel; a block in which a flow passage connecting among the syringes, the capillary and a buffer reservoir is formed; a check valve for preventing the gel from flowing back to the charging syringe, the check valve being arranged between the charging syringe and the flow passage; and an encoder for obtaining an amount of the gel in the injection syringe.

(6) The electrophoretic instrument further comprises a light source for exciting the electrophoretically separated sample; and a detector for detecting fluorescence generated by the excitation.

(7) The electrophoretic instrument, wherein the flow passage of the block is composed of a first flow passage communicating between the charging syringe and the injection syringe, and a second flow passage communicating between the injection syringe and the capillary.

(8) The electrophoretic instrument, wherein a branching passage to the buffer reservoir is provided at a middle position of the second flow passage, an electrode used at performing electrophoresis being inserted into the buffer reservoir.

(9) The electrophoretic instrument further comprises motors for driving the injection syringe and the charging syringe.

(10) The electrophoretic instrument further comprises a control unit for controlling a driving amount and sequence of the motor using a signal of the encoder.

(11) The electrophoretic instrument, wherein it is detected from a signal of the encoder that the plunger of the syringe is in contact with a drive unit.

DESCRIPTION OF THE PREFERRED EMBODIMENTS

An embodiment of an electrophoretic instrument in accordance with the present invention will be described below, referring to the accompanied drawings.

Figure 1:
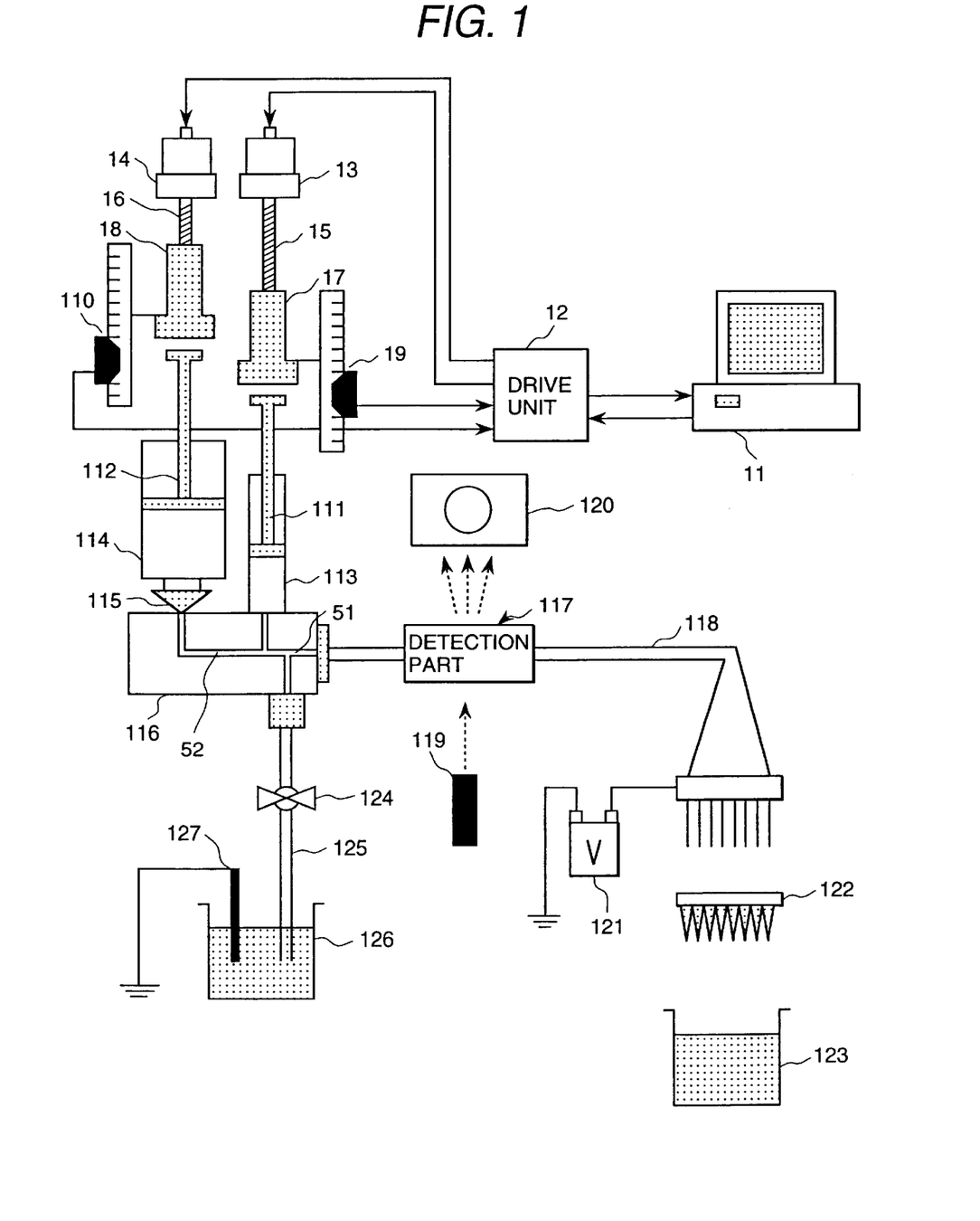
FIG. 1a is a schematic view showing the overall structure of an embodiment of an electrophoretic instrument in accordance with the present invention.
FIG. 1b is a schematic view showing the structure of a capillary array of the above-described embodiment of the electrophoretic instrument.
Figure 1B:
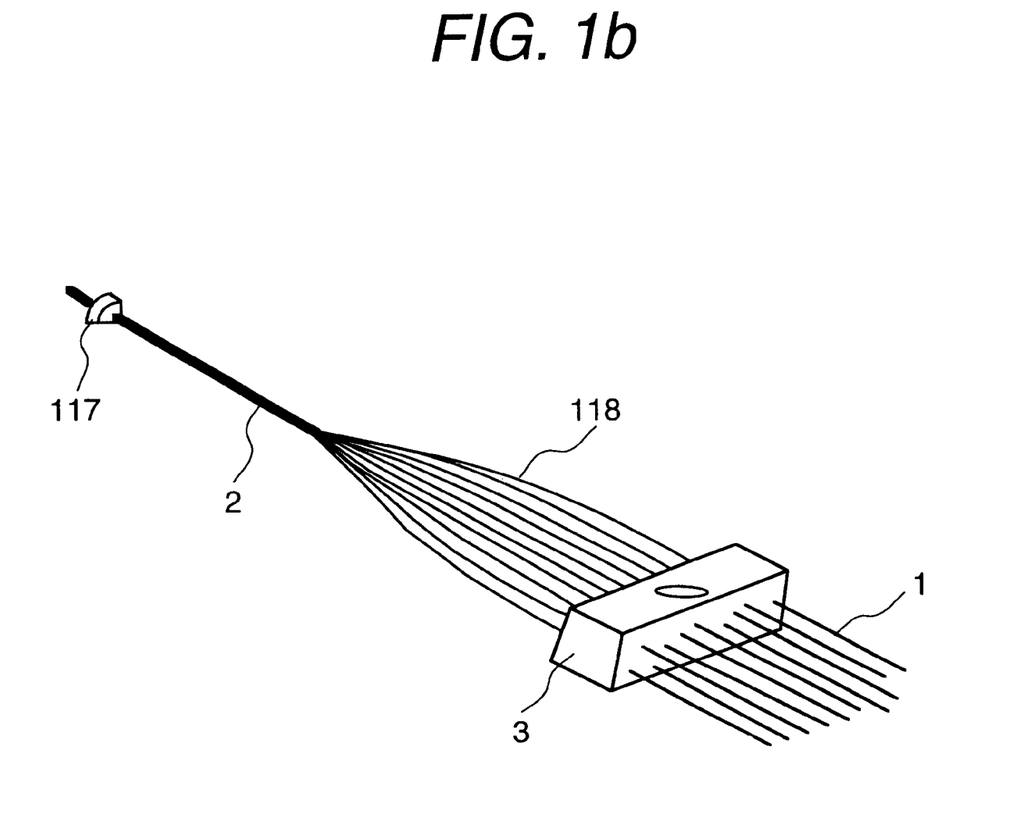

FIG. 1a is a view showing the overall structure of an embodiment of an electrophoretic instrument in accordance with the present invention. Number of capillary formed of quartz tubes is at least one or more. In this embodiment, a capillary array 118 is formed using a plurality of capillaries. One end of each of the capillaries containing the injected gel, not shown, is inserted into each of sample containers 122 in order to supply a sample to the capillary, and the capillaries in the other end side are bundled together before a detection part 117, and the ends of the bundle of the capillaries passing through the detection part 117 are inserted to a block 116 through a junction portion. FIG. 1b is a schematic view showing the capillary array, and the bundle portion of the array in the gel supplying side is inserted to the block, or the junction portion is joined with the flow passage of the flow passage. A cylindrical electrode 1 covering each of the capillaries is provided in the sample supply side of the capillaries. A common electrode 3, not shown, is integrally arranged in an array holder 3 so that the common electrode and the cylindrical electrodes 1 are connected to an electric power source 121 when the capillary array is attached to the array holder 3. The pairs of the capillary and the cylindrical electrode are inserted into sample containers 122 or a buffer container 123 to absorb samples or a buffer solution into the capillaries by the electrophoretic action.

The capillary 118 is filled with a gel of a medium for separating a sample from the block 116 side before starting measurement. The outer surface of each of the capillaries is coated with a polyimide film in order to improve its mechanical strength, but the polyimide film at a position of the detector is peeled and removed off from the capillary so as to transmit excited light through the capillary and to extract generated fluorescence.

A gel injection mechanism is composed of the block 116, an injection syringe 113, a charging syringe 114 and a check valve 115. The injection syringe 113 for injecting the electrophorsis medium gel such as a polymer gel into the capillaries 118 and the charging syringe 114 for charging the injection syringe 113 with the gel are attached to the block 116.

The inside of the block 116 is composed of a first flow passage 52 communicating between the charging syringe 114 and the injection syringe 113 and a second flow passage 51 communicating between the injection syringe 113 and the capillaries 118. A branching passage to a buffer reservoir 126, which is to be in ground electric potential when performing electrophoresis, is provided at a position in the middle of the second flow passage. Further, a check valve 115 is inserted between the charging syringe 114 and the first flow passage 52 to prevent the gel from flowing back to the charging syringe 114.

The charging syringe 114 and the injection syringe 113 are pressed by driving motors 13, 14 controlled by a control unit 12 to move down drive units 17 and 18 attached to actuators 15, 16, respectively. Encoders 19 and 110 are attached to the drive units 17 and 18, respectively. Positional information of the drive units 17 and 18 obtained by reading values of the encoders is transmitted to the computer 11 through the control unit 12.

The capillary array 118 is moved to a sample container 122 after being filled with the gel, and then moved to a buffer container 123 after sucking a sample by an electric action. As an voltage is applied to the buffer container 123 through the electrode portion of the capillaries, an electric field is produced between the buffer container 123 and the buffer reservoir 126, and as the result, the samples in the capillaries are started to be electrophoresed.

The introduced sample is separated because the electrophoretic mobility of a molecule differs depending on its molecular weight and so on, and therefore, the separated samples are detected at the detection part 117. Since the sample is labeled with a fluorescent substance in advance, the fluorescent substance is excited by a light source 119 at a detection part 117, and the fluorescence generated at that time is detected by a photo-detector 120 such as a CCD camera or the like. Particularly, in a case of a deoxyribonucleic acid (DNA) sample, the base of terminal of the sample can be identified from the wavelength of the detected fluorescence by labeling the sample with specific fluorescent substances depending on the bases of terminal of the DNA such as adenine, guanine, thymine and cytosine. After completion of the analysis, the gel in the capillary array 118 is replaced by the new gel by the injection syringe 113, and then the next measurement is started again.

Figure 2:
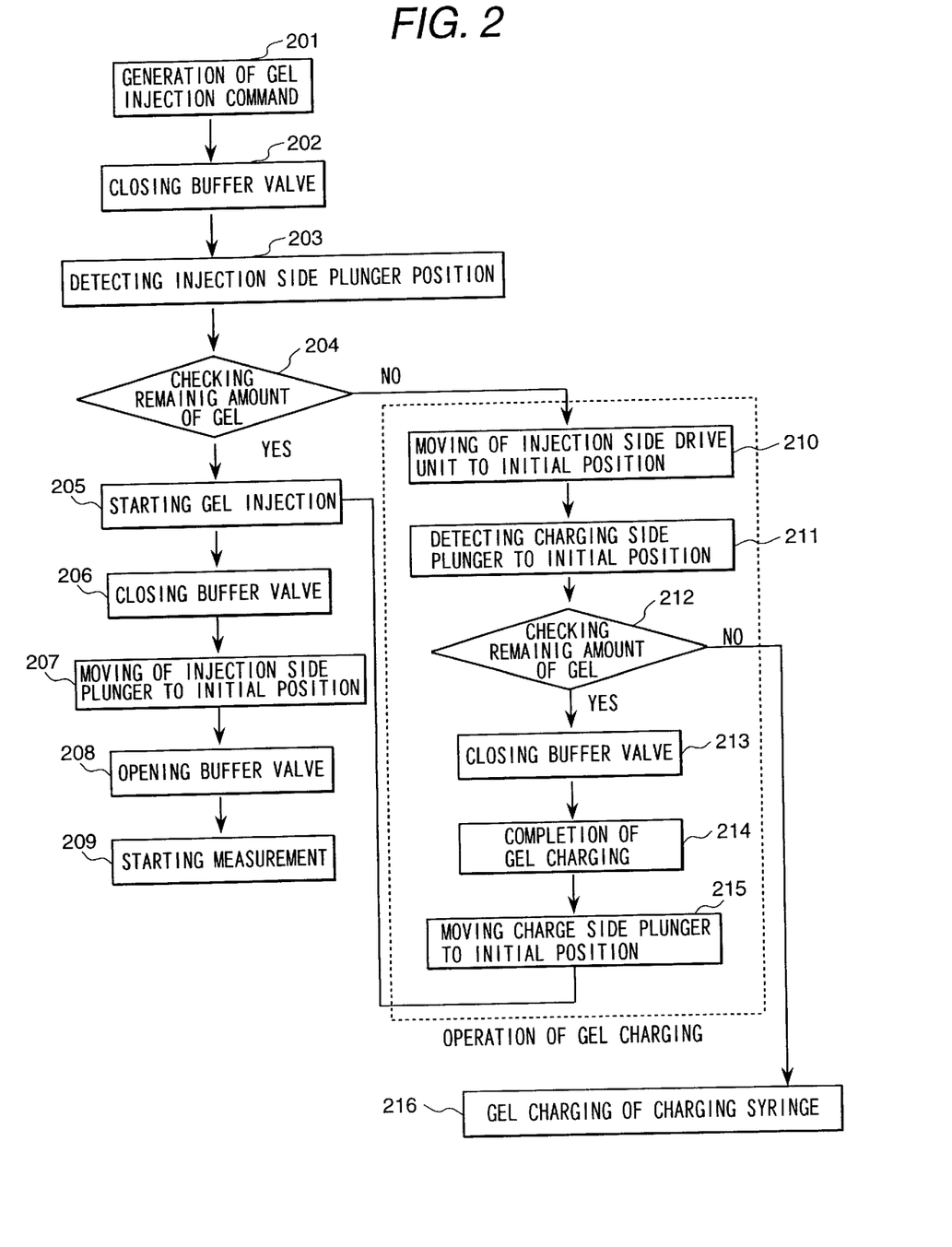
FIG. 2 is a flowchart showing the gel charging operation in the electrophoretic instrument of FIG. 1.

FIG. 2 is a flowchart showing the gel charging operation. The control unit 12 receiving a command of gel injection from a computer 11 (201) initially closes a buffer valve 124 (202). After that, the drive unit 17 is moved down to automatically detect a position of a plunger 111 of the injection syringe 113 (203). An amount of gel remaining in the injection syringe 113 can be checked from a value of the linear encoder 19 in the injection side at that time (204). If the amount of the gel in the injection syringe 113 is insufficient, operation of charging the injection syringe 113 with the gel from the charging syringe 114 is performed in prior to gel injection to the capillary array 118.

The gel charging operation is performed as following. The drive unit 17 in the injection side is moved to a position corresponding to a position of the plunger 111 of the injection syringe 113 at the time when the injection syringe 113 is filly filled with the gel (210). Then, the drive unit 18 in the charging side is moved down to a position of the plunger 112 of the charging syringe 114 (211), and an remaining amount of the gel is checked from a value of the encoder 110 in the charging side (212). If the remaining amount is sufficient, the charging syringe 114 is stared to be pressed to start gel charging (213). At that time, almost all of the gel pushed out from the charging syringe 114 and flowing into the block 116 flows into the injection syringe 113 while pushing up the plunger 111 of the injection syringe 113, but does not flow into the capillaries due to difference between the flow-resistance values of the flow passages. When the injection syringe 113 is filled with the gel, the plunger 111 contacts with the drive unit 17 in the injection side to be stopped, and the gel charging is completed (214). After completion of the gel charging, the drive unit 18 in the charging side is moved upward in order to release the pressure, and stands by until the next command is generated (215). If the amount of the gel remaining in the charging syringe 114 is insufficient, a message of shortage of the remaining amount is displayed on the screen of the computer 11, and the operation of gel charging is restarted after charging the charging syringe 114 with the gel (216).

When the amount of the gel remaining in the injection syringe 113 is sufficient or when the gel charging is completed, the drive unit 17 in the injection side is started to press the injection syringe 113 to start gel injection to the capillaries 118 (205). At that time, the check valve 115 prevents the gel from flowing back to the charging syringe 114. Further, since the buffer valve 124 is closed, the gel pushed out from the injection syringe 113 flows into the capillaries 118 of only one flow passage to which the gel can flow out. The gel injection is completed when a certain mount of the gel is charged into the capillary, and the drive unit 17 in the injection side is stopped to press the injection syringe 113 (206), and moved upward in order to release the pressure, and stands by (207). Further, after the buffer valve 124 is opened (208), voltage is applied to the electrode portion of the capillaries to start electrophoresis (209).

Figure 3:
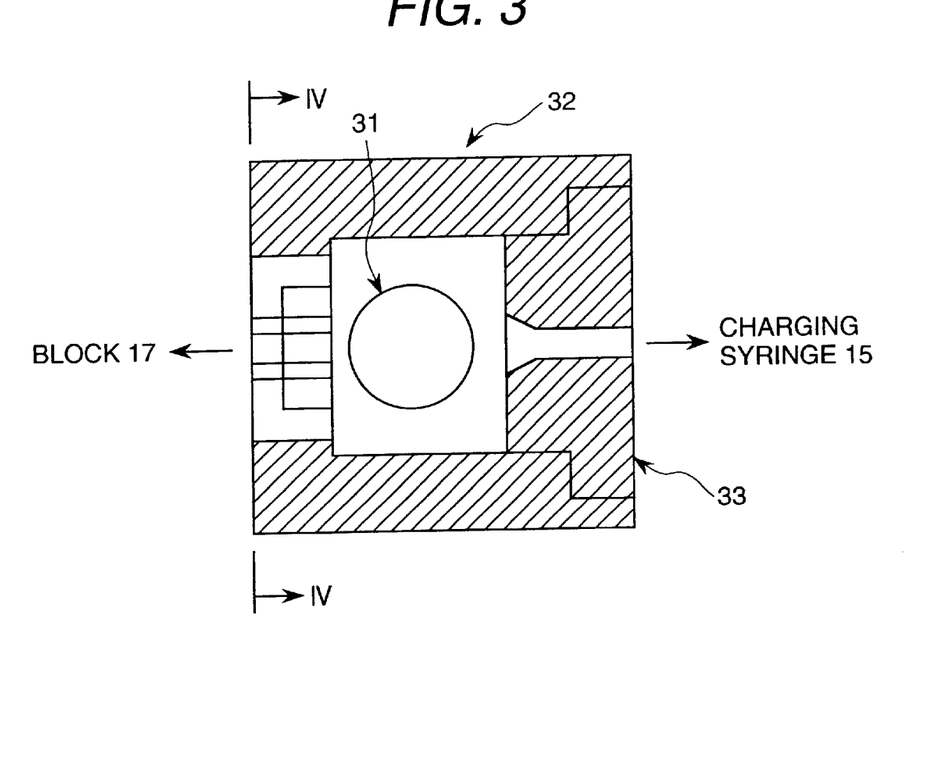
FIG. 3 is a cross-sectional view showing a check valve inserted between a charging syringe and a first passage.
Figure 4:
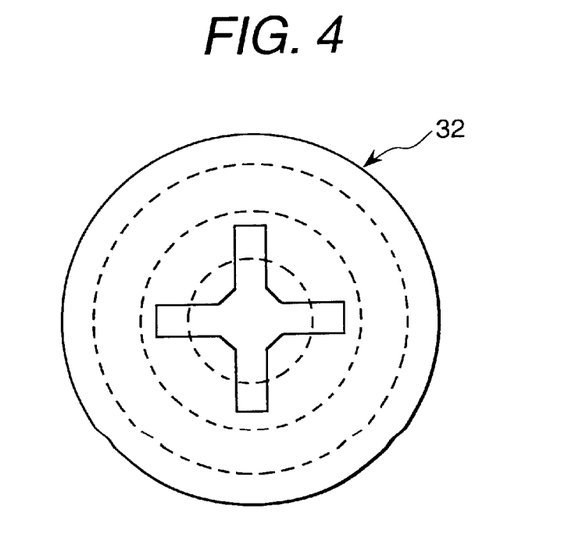
FIG. 4 is a front view of the check valve of FIG. 3 seeing from the block side.

Next, an embodiment of the check valve 115 used in the present invention is shown in FIG. 3 and FIG. 4. FIG. 3 shows a cross-sectional view when the check valve 16 is divided along the flow passage, and FIG. 4 show a front view when the check valve 115 is seen from the block side. When the gel flows from the charging syringe 114 toward the block 116, a ball 31 is pushed against a groove portion of a ball stopper with grooves 32. At that time, the gel can flow from the charging syringe 114 toward the block 116 because the gel can flow through the outer portions of the groove of the ball stopper 32. On the other hand, when the gel flows from the block 116 toward the charging syringe 114, the ball 31 is pushed against a ball stopper 33 to completely close the flow passage. Therefore, the gel can not flow out. As the result, the back-flow preventive action of the check valve 115 works well.

Figure 5:
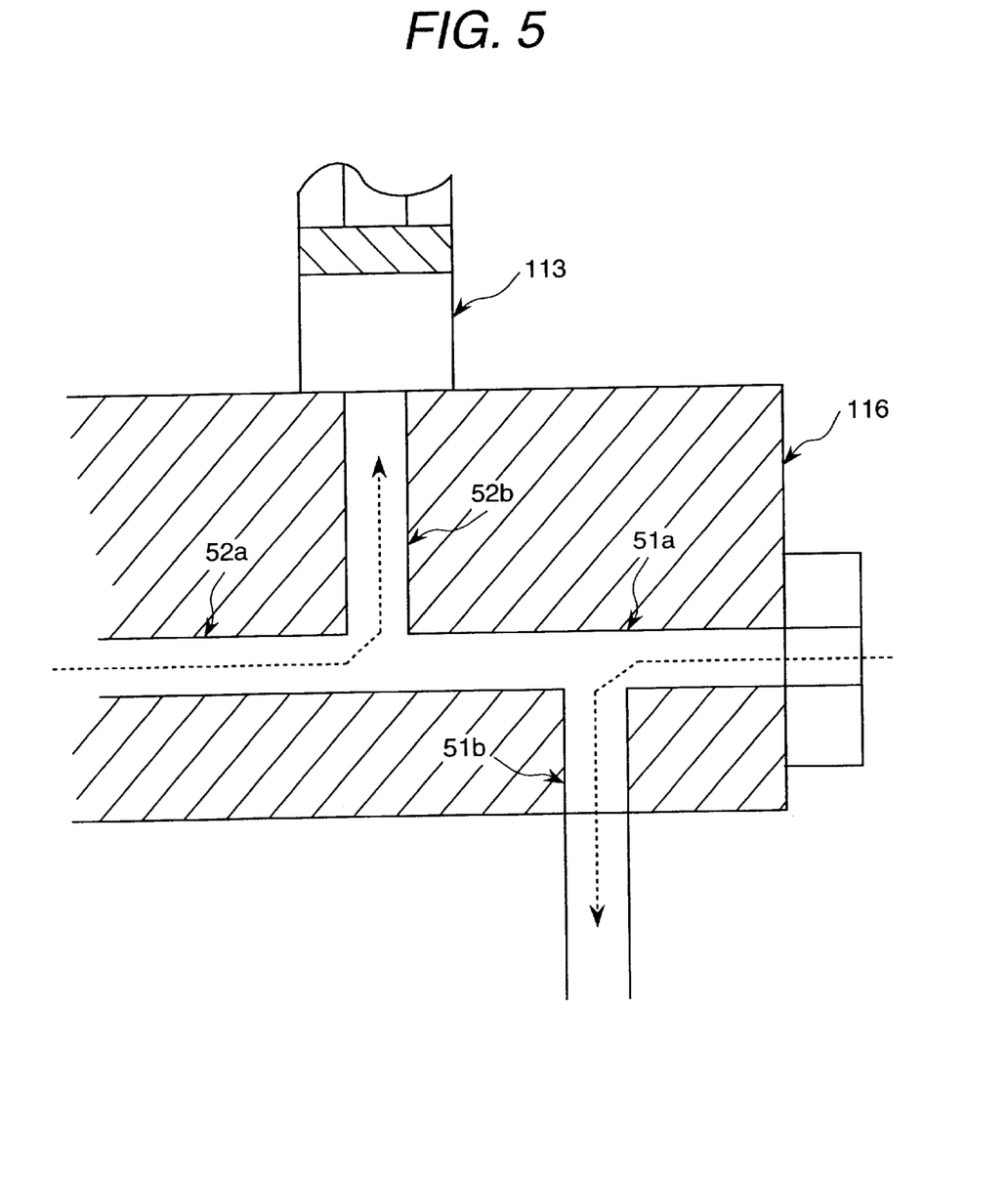
FIG. 5 is an enlarged view of the inner flow passage of the block.

FIG. 5 shows an enlarged view of the flow passage in the block. Since the sample and ionized impurities flowing from the capillaries 118 into the flow passage 51a in the block flows toward the buffer reservoir 126 into which the electrode 127 in the ground electric potential is inserted, the gel flows toward the flow passage 51b from the flow passage 51a. That is, since the first flow passage composed of the flow passage 52a and the flow passage 52b, which are used at gel charging, is completely independent from the electrophoretic lanes (notes: the electrophoretic lane is the path from the end of the capillary also serving as the cathode to the buffer reservoir also serving as the anode through the first flow passage 51a and the flow passage 51b), the impurities can be prevented from entering and mixing with the gel filling in the capillaries 118 (the gel in the first flow passage and the both syringes) in the following measurement and from then on.

Figure 6:
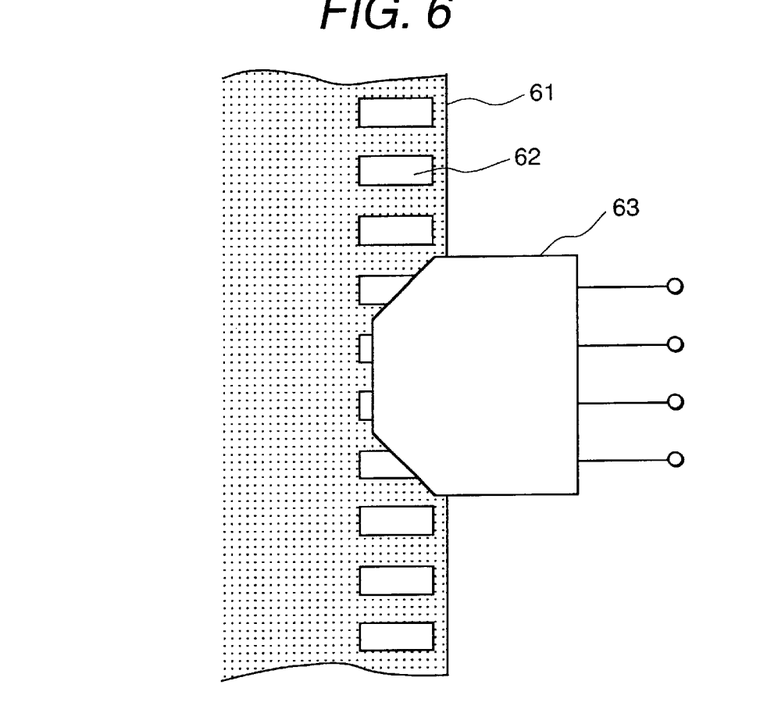
FIG. 6 is a schematic view showing a linear encoder.
Figure 7:
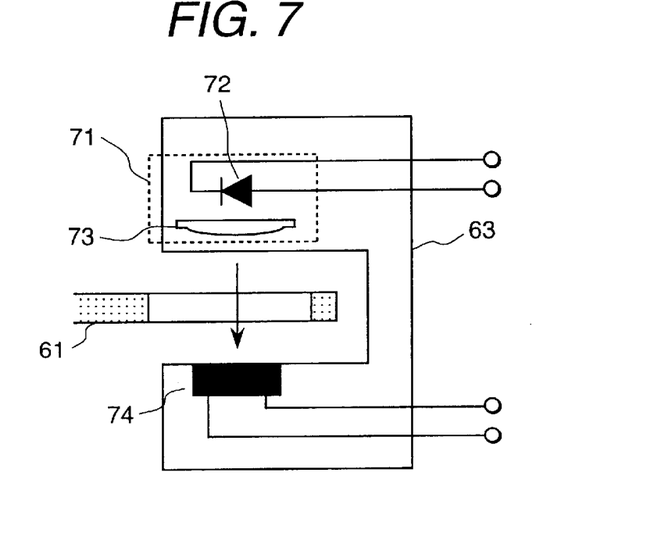
FIG. 7 is a conceptual view of an optical detector of the linear encoder.

The operation principle of the linear encoder will be described below, referring to FIG. 6 and FIG. 7. A film 61 having slits 62 formed on a straight line is attached to the drive unit, and the slits pass through a photo-detecting part 63 attached to the main body of the instrument when the drive unit is moved. The photo-detecting unit 63 is composed of a light source part 71 having a light-emitting diode 72 as a light source and a lens for forming a parallel light beam; and a photo-sensor 74. Thereby, number of the slits passing between the light source part 71 and the photo-sensor 74 can be optically counted. The control unit 12 can recognize a movement per unit time of the drive unit by periodically checking the number counted by the detecting unit 63, and a position of the drive unit at the present time can be also known from the total movement.

Figure 8:
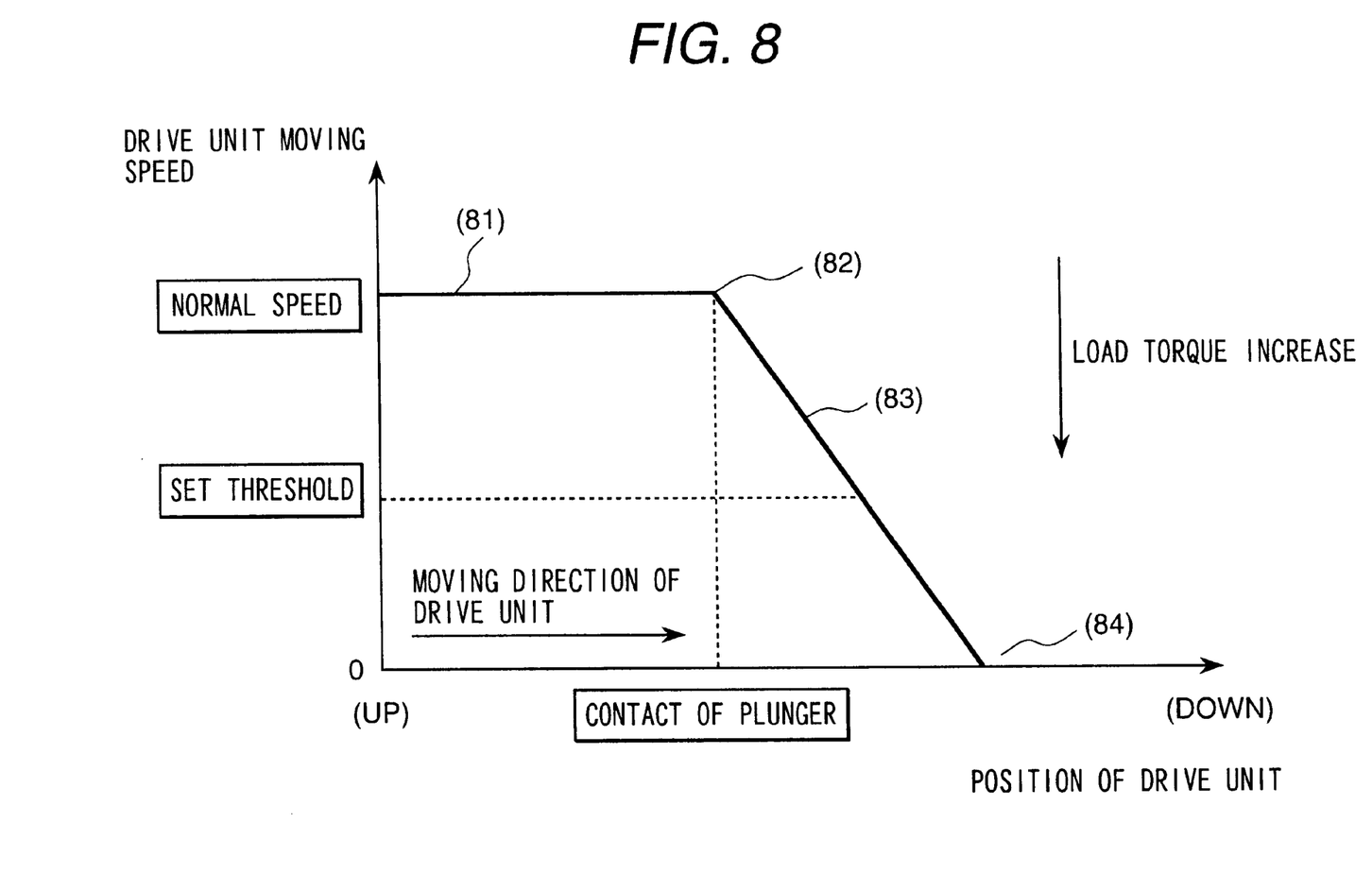
FIG. 8 is a diagram showing change in moving speed of a drive unit depending on the positional relation of the drive unit and a syringe.

The detection of a plunger position described in the operation of gel injection will be described below in detail. The detection of a plunger position means an operation of the drive unit automatically moving down to the position of the plunger using a characteristic of a DC motor that the rotating speed varies depending on the magnitude of load. The operation principle will be described below, referring to FIG. 8. When the drive unit is being moved above the plunger, the main load is only the self-weight of the drive unit. Therefore, the drive unit is moved at a constant speed corresponding to the load described above (81). Then, the drive unit becomes in contact with the plunger (82). When the drive unit is about to further push the plunger from that state, a larger load acts on the drive unit due to increase of the inner pressure of the syringe. As the result, the rotating speed of the DC motor is drastically decreased (83), and the motor is finally locked to stop motion of the drive unit (84). Therefore, by setting a threshold at a speed slower than the normal speed of the drive unit described above, it is possible to judge whether or not the drive unit is in contact with the plunger. Actually, the value of the linear encoder is checked at a preset cycle, and when the movement of the drive unit becomes smaller than a preset threshold, it is judged that the drive unit is in contact with the plunger.

According to the embodiment described above, since the check valve is inserted between the charging syringe and the injection syringe, operation of switching the valve between gel charging and gel injecting is not necessary.

What is claimed is:

1. An electrophoresis method comprising the steps of supplying a gel for electrophoresis to a bore of an injection syringe; driving a plunger of said injection syringe by a motor; injecting the gel into a bore of a capillary through a block having a flow passage communicating to said capillary; and supplying a sample to be analyzed to said capillary, and separating said sample by electrophoresis, the method further comprising the steps of:

detecting the amount of the gel remaining in said injection syringe;

driving a plunger of a charging syringe to charge said flow passage in said block with the gel from the charging syringe when the value of the amount of gel detected is smaller than a predetermined amount of the gel that should be in the injection syringe, the charging syringe being connected to said flow passage in aid block through a check valve; then supplying the gel in said in injection syringe to said capillary by the plunger of said injection syringe.

2. An electrophoresis method according to claim 1, wherein said capillary is a capillary array having a plurality of capillaries, and a sample is electrophoretically moved through the capillaries from sample supply ends of the capillaries, each of said supply ends serving as a cathode of a capillary in said array, toward a buffer reservoir serving as an anode for all capillaries in said array.

3. An electrophoresis method according to claim 1, the method further comprising the steps of determining an amounts of the gel in said injection syringe and an amount of gel in said charging syringe using encoders; injecting an amount of the gel necessary for one electrophoresis into said capillary; then checking an amount of the gel remaining in said injection syringe; and supplying an amount of the gel necessary for subsequent electrophoreses from said charging syringe into said injection syringe as required.

4. An electrophoresis method according to claim 1, the method further comprising the steps of exciting the sample separated by the electrophoresis using an electromagnetic wave; and detecting fluorescence generated by the excitation.

5. An electrophoretic instrument comprising:
a capillary;
a buffer reservoir;
a gel injection mechanism for injecting a gel of a sample separating medium into said capillary comprising:
an injection syringe with a plunger for injecting gel into said capillary;
a charging syringe with a plunger for performing charging with gel;
a block having a flow passage that connects said injection syringe, said charging syringe, said capillary and said buffer reservoir; and
a check valve for preventing gel from flowing back to said charging syringe, said check valve being arranged between said charging syringe and said flow passage; and
an encoder for determining an amount of gel in said injection syringe; and
a detecting unit for detecting a sample introduced into said capillary and electrophoretically separated.

6. An electrophoretic instrument according to claim 5, which further comprises a light source for exciting the electophoretically separated sample; and a detector for detecting fluorescence generated by the excitation.

7. An electrophoretic instrument according to claim 5, wherein said flow passage of said block is composed of a first flow passage communicating between said charging syringe and said injection syringe, and a second flow passage communicating between said injection syringe and said capillary.

8. An electrophoretic instrument according to claim 7, wherein a branching passage to said buffer reservoir is provided at a middle position of said second flow passage, and an electrode for performing electrophoresis has been inserted into said buffer reservoir.

9. An electrophoretic instrument according to claim 5, which comprises motors for driving said injection syringe and said charging syringe.

10. An electrophoretic instrument according to claim 9, which comprises a control unit for controlling a driving amount and sequence of said motor using a signal of said encoder.

11. An electrophoretic instrument according to claim 10, wherein a signal of said encoder indicates that the plunger of said syringe is in contact with a drive unit.

12. An electrophoretic instrument comprising:
a capillary;
a buffer reservoir;
a gel injection mechanism or injecting a gel of a sample separating medium into said capillary comprising:
an injection syringe with a plunger for injecting gel into said capillary;
a charging syringe with a plunger for performing charging with gel;
a block having a flow passage that connects said injection syringes, said charging syringe, said capillary and said buffer reservoir; and
a check valve for preventing gel from flowing back to said charging syringe, said check valve being arranged between said charging syringe and said flow passage; and
an encoder for detecting positional information of a drive unit; and
a detecting unit for detecting a sample introduced into said capillary and electrophoretically separated.

* * * * *